United States Patent
Atchison

(10) Patent No.: US 9,562,839 B2
(45) Date of Patent: Feb. 7, 2017

(54) SCOOP ASSEMBLY AND METHOD

(71) Applicant: Martin Atchison, Manvel, TX (US)

(72) Inventor: Martin Atchison, Manvel, TX (US)

(*) Notice: Subject to any disclaimer, the term of this patent is extended or adjusted under 35 U.S.C. 154(b) by 175 days.

(21) Appl. No.: 14/187,901

(22) Filed: Feb. 24, 2014

(65) Prior Publication Data

US 2014/0239630 A1  Aug. 28, 2014

Related U.S. Application Data

(60) Provisional application No. 61/769,896, filed on Feb. 27, 2013.

(51) Int. Cl.
| | | |
|---|---|---|
| *F16L 9/00* | (2006.01) | |
| *F16L 27/00* | (2006.01) | |
| *F16L 41/14* | (2006.01) | |
| *G01N 9/36* | (2006.01) | |
| *F16L 41/08* | (2006.01) | |
| *G01N 1/20* | (2006.01) | |
| *F16L 41/10* | (2006.01) | |

(52) U.S. Cl.
CPC . *G01N 9/36* (2013.01); *F16L 9/00* (2013.01); *F16L 27/00* (2013.01); *F16L 41/08* (2013.01); *F16L 41/084* (2013.01); *F16L 41/10* (2013.01); *G01N 1/20* (2013.01); *G01N 1/2035* (2013.01); *Y10T 137/0402* (2015.04); *Y10T 137/598* (2015.04)

(58) Field of Classification Search
CPC .................................... F16L 9/00; F16L 41/14
USPC .......................................................... 73/426
See application file for complete search history.

(56) References Cited

U.S. PATENT DOCUMENTS

| | | |
|---|---|---|
| 15,560 A | 8/1856 | Fetter |
| 1,101,574 A | 6/1914 | Shephard |
| 1,334,130 A | 3/1920 | Blanchard |
| 2,301,280 A | 11/1942 | Howe |
| 2,463,707 A | 3/1949 | Matousek |
| 2,503,826 A | 4/1950 | Robert |
| 2,508,763 A | 5/1950 | Mercier |
| 2,922,441 A | 1/1960 | Ferdinand |
| 2,926,527 A | 3/1960 | Crandall |
| 3,101,619 A | 8/1963 | Hunter |
| 3,776,274 A | 12/1973 | Riley |
| 4,018,089 A | 4/1977 | Dzula |
| 4,152,936 A | 5/1979 | Boykin |

(Continued)

OTHER PUBLICATIONS

Brad Frank, Save Money When Ordering Tools, TheFabricator.com/ The Tube & Pipe Journal, Nov. 21, 2002, Issue 431, USA.

(Continued)

*Primary Examiner* — Lisa Caputo
*Assistant Examiner* — Jamel Williams
(74) *Attorney, Agent, or Firm* — Kenneth L. Nash

(57) ABSTRACT

The present invention describes a tubular scoop that may be utilized with various assemblies for sampling fluid in a pipeline. The scoop includes a bend with a bend radius that is from two to four times the diameter of the scoop. The scoop defines a scoop face that is parallel to an axis of the tubular of the scoop. The scoop is mounted with a threaded connection that seals around the tubular. An additional seal comprises a compression nut that allows orientation of the scoop within the pipeline whereupon the scoop orientation is fixed by tightening the compression nut.

24 Claims, 9 Drawing Sheets

(56) References Cited

U.S. PATENT DOCUMENTS

| | | | |
|---|---|---|---|
| 4,391,152 A | 7/1983 | Ellett | |
| 4,606,218 A | 8/1986 | Chisman, III | |
| 4,631,967 A | 12/1986 | Welker | |
| 4,633,713 A | 1/1987 | Mesnard | |
| 4,717,159 A | 1/1988 | Alston | |
| 4,776,618 A | 10/1988 | Barree | |
| 4,928,536 A | 5/1990 | Welker | |
| 5,009,113 A | 4/1991 | Kamrat | |
| 5,138,755 A | 8/1992 | Evans | |
| 5,161,417 A | 11/1992 | Strong | |
| 5,410,920 A | 5/1995 | Westwick | |
| 5,974,858 A | 11/1999 | Francisco, Jr. | |
| 7,066,496 B2 | 6/2006 | Williams | |
| 8,647,483 B2 | 2/2014 | Andrews | |
| 2003/0070718 A1 | 4/2003 | Benham | |
| 2004/0161804 A1* | 8/2004 | McCash | A61B 5/097 435/7.2 |
| 2009/0145488 A1* | 6/2009 | Hoskisson | F16L 41/06 137/318 |
| 2014/0251007 A1* | 9/2014 | Atchison | F16L 9/00 73/32 R |
| 2014/0252759 A1* | 9/2014 | Atchison | F16L 9/00 285/144.1 |

OTHER PUBLICATIONS

Compression Fitting, Wikipedia, Feb. 5, 2016, Information Last Updated Nov. 2, 2015, USA.
Don Sextro, Installation and Operation of Densitometers, Targa Resources, Houston, Texas, USA.
Oil and Gas Pipelines, Tenaris Technical Information Page (www.tearis.com/en/Products/OnshoreLinePipe/OilandGasPipeline.aspx), Feb. 5, 2016.
Why Steel: Strength, Toughness, Ductility and Weldability, Why Steel, Feb. 5, 2016.
Pipelines, OnePetro.org, Feb. 5, 2016.
Seamless Pipe, Drilling Lexicon, iadlexicon.org, Feb. 5, 2016.
SAF T FLO, Instruction manual: Retractable Sampling Probe, Apr. 4, 2012.
SAF T FLOW, Sampling Probes, Oct. 16, 2008, Archived Version.
Swagelok, An Installer's Pocket Guide for Swagelok Tube Fittings, Mar. 2004.
Swagelok, Sample Probe Module Application Guide, Sep. 2011, pp. 12-14.

* cited by examiner

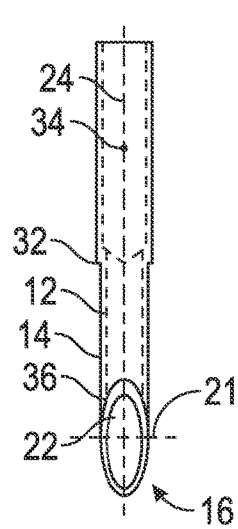
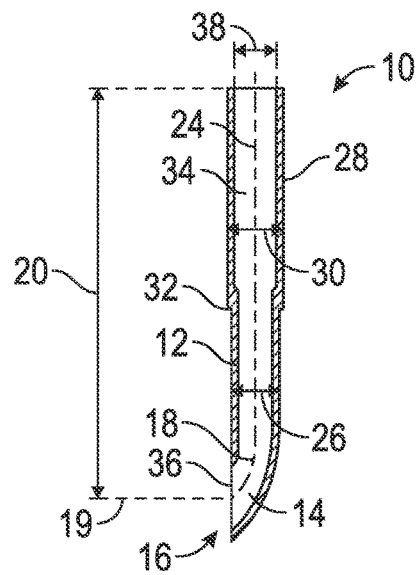
FIG. 1A  FIG. 1B
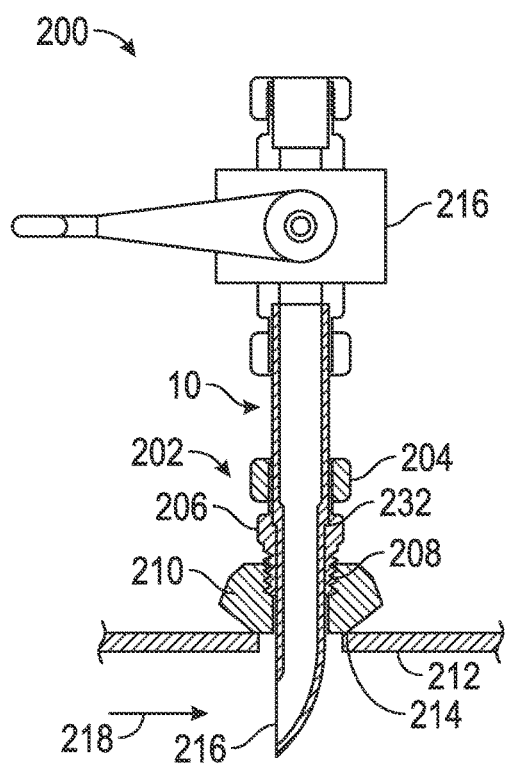
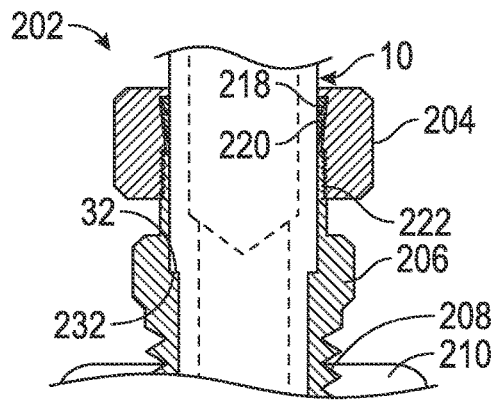
FIG. 2A  FIG. 2B

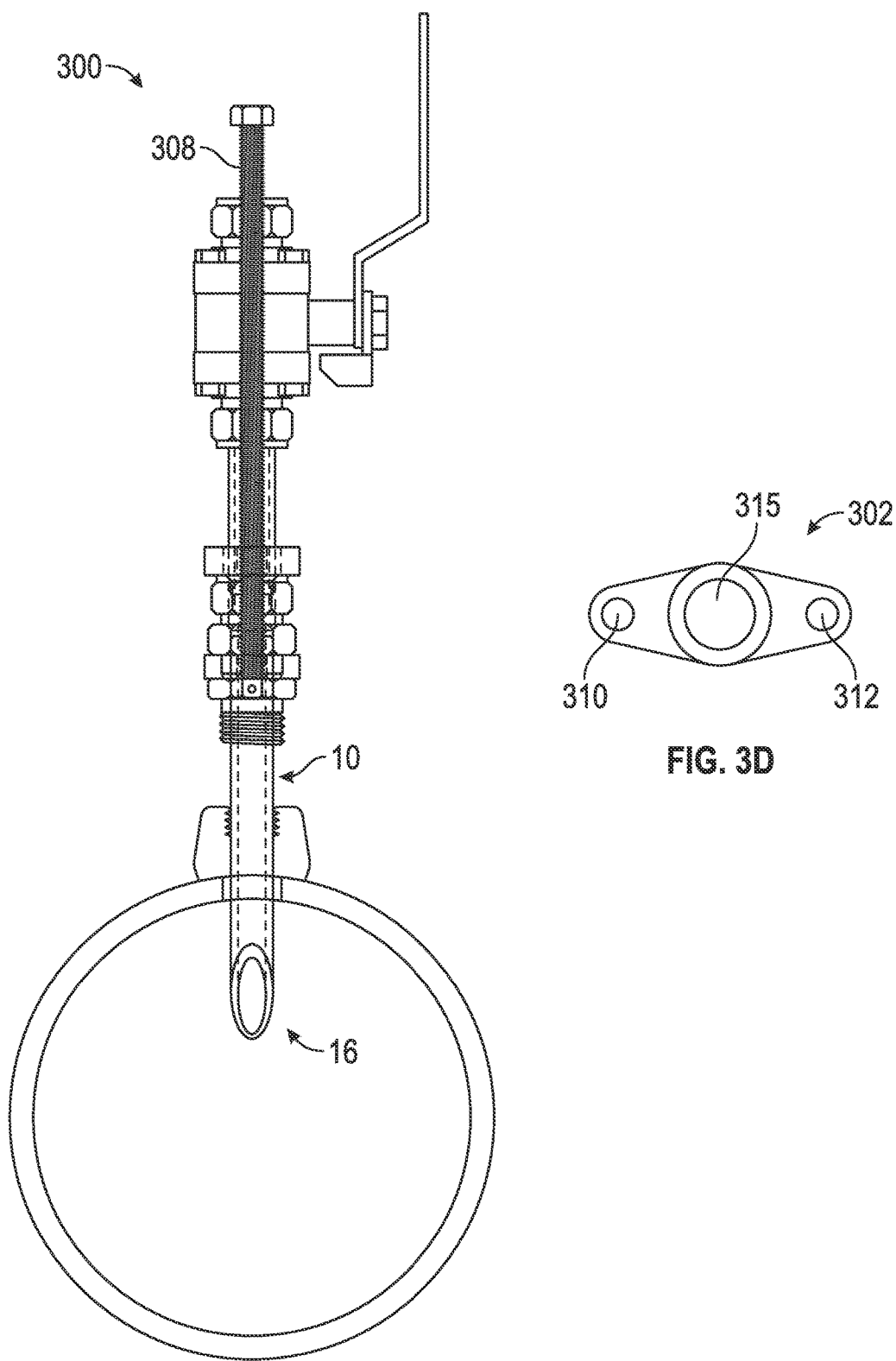

SCOOP ASSEMBLY AND METHOD

This application claims benefit of U.S. Provisional Patent Application No. 61/769,896 filed Feb. 27, 2013.

CROSS REFERENCE TO OTHER PATENT APPLICATIONS

None.

BACKGROUND OF THE INVENTION (1) Field of the Invention

The present invention relates generally to scoops for measuring the density of fluid in pipelines and, more specifically, in one or more embodiments to novel scoop configurations that provide improved flow and more accurate density readings of the fluid.

(2) Background of the Invention

Scoops have been utilized for decades to monitor the density of the fluids in pipelines. The density of the fluids relates to how much product is transported. Accuracy of the density readings is important because the result can affect the prices paid for shipping product through the pipeline, which prices can be significant. Therefore both the pipeline companies and the users of the pipelines desire to obtain the most accurate readings as possible.

Despite the long felt need for accurate readings, prior art scoops have long had many problems that have not been resolved. Prior art scoops may not produce enough fluid flow to obtain a good sample. In some cases, differential pressure devices such as pumps are required when using prior art scoops. Differential pressure devices can introduce fluid contamination as well as increase the size and complexity of the density measurement systems.

Scoops used to take samples can be inaccurate because fluid beneath the valve is static. Therefore the sample taken may not be representative of fluid in the pipeline at the moment the sample is taken and/or can be contaminated with fluid that has accumulated beneath the valve.

In some cases, scoops are mounted utilizing a threaded receptacle that may be secured and sealed to the pipeline utilizing one of three sanctioned connections 1) pipe threads & sealant; 2) socket weld or 3) butt-weld. The threads in the threaded receptacle provide a seal with the threaded receptacle. However, mounting the scoop to the threaded receptacle can provide difficulties in orienting in the pipe in a manner that maximizes flow through the scoops.

Another problem is that scoops must on occasion be removed from the pipeline to allow pigs to pass through the pipeline. Removing and reintroducing the scoops can be time consuming with corresponding lost use of the pipeline.

Those of skill in the art have long sought a better scoop design and better scoop systems to provide more accurate readings. Consequently, those of skill in the art will appreciate the present invention, which addresses the above and/or other problems.

SUMMARY OF THE INVENTION

Accordingly, it is an object of the present invention to provide improved scoop designs.

Another possible object of the invention is to provide a scoop design that is compact and improves flow of product through the scoop.

Yet another object of the invention is to provide a scoop design that bends a pipe so the pipe remains straight but the face of the scoop is directed laterally into the flow.

Yet another object of the invention is to provide a scoop design utilizing a tubular to pipe connector wherein the pipe connector threads onto a mating threaded connector on the pie but provides a compressible connection that allows rotation of the scoop for orientation of the scoop prior to tightening of the connector.

Yet another object is providing a retractable pipe scoop design.

Yet another object is to provide a compact bi-directional tandem scoop design.

Yet another object is to provide an even more compact single scoop pipe bi-directional scoop design.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 1A is a front elevational view, partially in hidden lines, of a scoop to obtain a product sample in accord with one possible embodiment of the present invention.

FIG. 1B is a side elevational view, in cross-section, of the scoop of FIG. 1A in accord with one possible embodiment of the present invention.

FIG. 2A is a side elevational view, partially in cross-section, showing the scoop of FIGS. 1A and 1B mounted to a pipe utilizing a tubular to pipe connection in accord with one possible embodiment of the invention.

FIG. 2B is an enlarged elevational view, in cross-section, showing a tubular to pipe in accord with one possible embodiment of the invention.

FIG. 3C is a front elevational view, partially in hidden lines, showing the retractable scoop and yoke design of FIGS. 3A and 3B prior to mounting a threaded connector to the pipe connector in accord with one possible embodiment of the invention;

FIG. 3D is a top view of a yoke component for a retractable scoop in accord with one possible embodiment of the present invention.

Figure 3A:
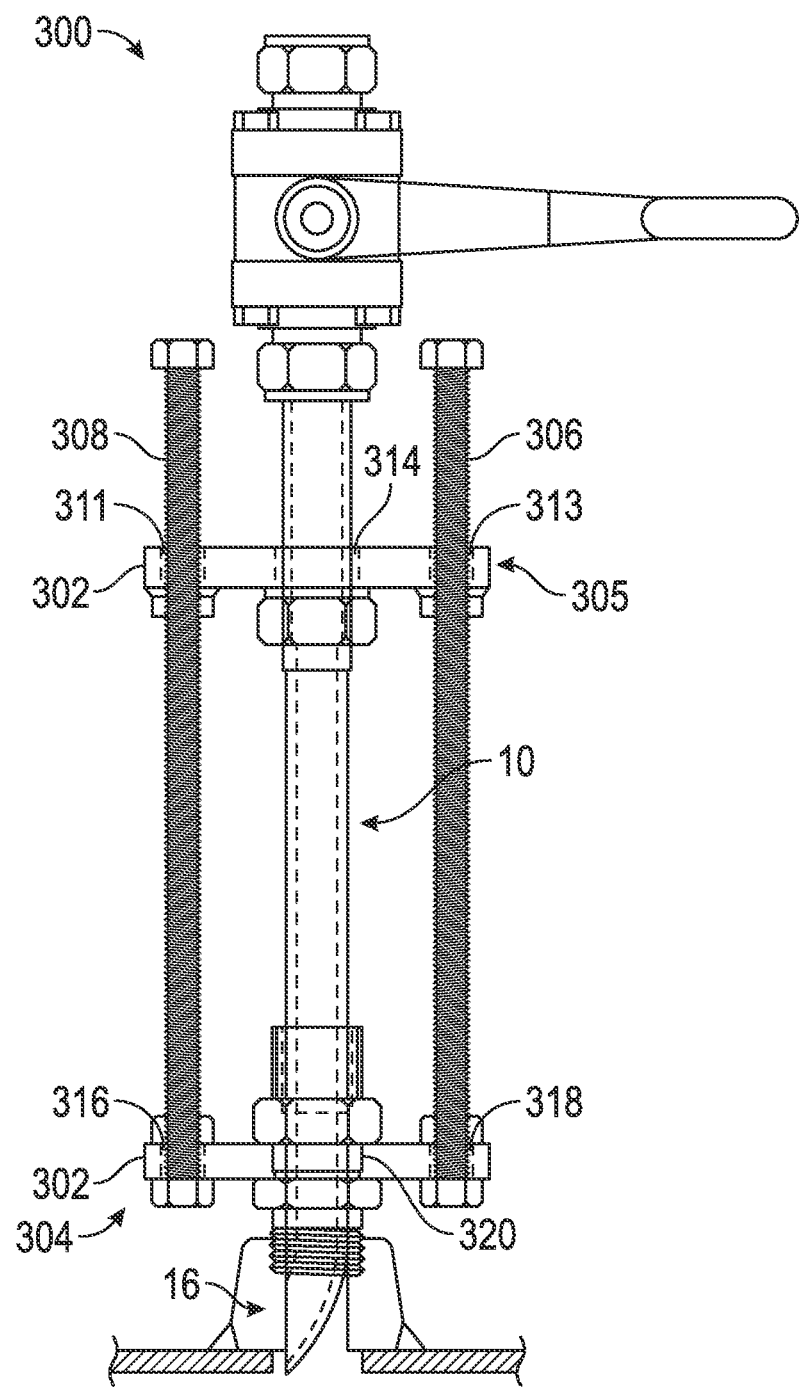
FIG. 3A is a side elevational view, partially in cross-section, showing a retractable scope and yoke design that in a retracted position with respect to a pipeline in accord with one possible embodiment of the present invention.

A sample scoop mountable to a pipeline for receiving flow from the pipeline, the pipeline being operable for transmitting at least one of liquid oil, oil, gas, or petroleum products, the sample scoop, the sample scoop comprising a tubular comprising a first tubular portion adjacent a scoop end; and a bend on an end most surface of the scoop end in the first tubular portion and a corresponding centerline of the tubular to form a scoop opening at the scoop end, the bend comprising a bend radius with a range between two times and four times a diameter of the first tubular portion, the opening in the scoop end forms a scoop face, the scoop face comprising at least a scoop face portion that is coaxial with a straight portion of the first tubular portion, the scoop face is elliptical in shape.

The sample scoop comprising a second tubular portion of the tubular, the second tubular portion comprising an increased diameter as compared to the first tubular portion with a shoulder between the first tubular portion and the second tubular Portion, The sample scoop further comprising a mark on at least one of the first tubular portion or the second tubular portion that is aligned with the scoop opening that visually indicates an orientation of the scoop opening with the pipeline when the sample scoop is mounted to the pipeline.

The sample scoop further comprising a compression nut and ferrule, the compression nut and the ferrule being mounted in surrounding relationship with the first tubular portion, the compression nut being operable to seal around the tubular while at least initially permitting rotation of the scoop end with respect to the pipeline, the compression nut being tightenable to thereby affix the orientation of the scoop opening within the pipeline.

A scoop mountable to a pipeline for receiving flow from the pipeline, the pipeline being operable for transmitting at least one of liquid oil, oil, gas, or petroleum products, the sample scoop, the scoop comprising: a tubular comprising a first tubular portion adjacent a scoop end; an opening in the scoop end that forms a scoop face, the scoop face comprises an outline that defines a plane that opens laterally with respect to the first tubular portion, the plane being parallel to a straight portion of an axis of the first tubular portion; a bend in the axis of the first tubular portion leading to the opening; and a seal member and a compression nut, the compression nut and the seal member being mounted in surrounding relationship with the first tubular portion, the tubular comprising a smooth surface for sealing with the seal member.

The scoop of wherein the plane comprises a plane portion that is substantially collinear to one side of the first tubular portion with the straight portion of an axis, the tubular being a seamless tubular.

The scoop wherein the scoop face is elliptical.

The scoop wherein a smaller axis of the scoop face is substantially equal to an internal diameter of the first tubular portion with the straight portion of an axis.

The scoop wherein the bend comprises a bend radius with a range of between two times and four times a diameter of the first tubular portion.

The scoop wherein the seal member comprises a ferrule, the ferrule and the compression nut being operable to seal around the tubular while at least initially permitting rotation of the scoop end with respect to the pipeline prior to finally tightening the compression nut to thereby affix an orientation of the scoop end within the pipeline.

A sample scoop mountable to a pipeline receptacle for receiving flow from a pipeline, the pipeline being operable for transmitting at least one of liquid oil, oil, gas, or petroleum products, the sample scoop, the sample scoop comprising: a tubular comprising a bend and defining a scoop opening, the scoop opening being directed laterally with respect to an axis through the tubular, the tubular being sized for insertion through the pipeline receptacle into the Pipeline for sampling the flow from the pipeline; a first seal comprising a compression nut and a ferrule, the tubular comprising a smooth surface, the compression nut and the ferrule each being mounted in surrounding relationship to the smooth surface of the tubular, the compression nut and the ferrule and the smooth surface cooperating to initially permit rotation of the tubular with respect to the pipeline to permit an orientation of the scoop opening with respect to the pipeline so that the scoop opening is orientable for alignment with an axis of the pipeline, the compression nut, the ferrule, and the smooth surface further cooperating so that the scoop opening is affixed in the orientation as the compression nut is tightened; and a connector attachable to the pipeline receptacle, the tubular being sized for insertion through the connector.

The sample scoop wherein the ferrule is compressible by the compression nut to form an initial seal with the smooth surface prior to the compression nut being fully tightened while initially permitting rotation of the tubular with respect to the pipeline to permit the orientation of the scoop opening with respect to the pipeline, the orientation with the pipeline maximizing fluid flow or fluid pressure into the scoop opening.

The sample scoop wherein the tubular comprises a first tubular portion comprising and a second tubular portion with an outer diameter larger than the first tubular portion to form a shoulder between the first tubular portion and the second tubular portion, a seat formed within the connector, the shoulder being adapted to mount on the seat.

The sample scoop further comprising an alignment marker on the tubular visible from outside the pipeline to visibly indicate the orientation of the scoop opening with respect to the pipeline.

The sample scoop further comprising the tubular and the connector are constructed so that a distance between the scoop opening and the shoulder provides that the scoop opening is positioned for sampling the fluid flow at least to a middle one third of the pipeline when the shoulder is in engagement with the seat.

The sample scoop wherein the tubular comprises a seamless tubular and the compression nut and the connector comprise mating threads to connect the compression nut to the connector.

The sample scoop wherein the pipeline receptacle comprises threads that mate to corresponding threads of the connector to form a second seal between the connector and the pipeline receptacle.

A method of using a sample scoop assembly mountable to a pipeline for receiving a fluid sample from the pipeline, the pipeline supporting fluid flow therethrough, a pipeline receptacle for mounting the sample scoop assembly to the pipeline, the pipeline being operable for transmitting at least one of liquid oil, oil, gas, or petroleum products, the method comprising the steps of: attaching a connector to the pipeline receptacle; inserting a tubular through the connector and the pipeline receptacle, the tubular comprising a scoop opening that opens laterally with respect to an axis through the tubular; after the inserting and the attaching, then orienting the scoop opening with respect to the pipeline utilizing an alignment marker on the tubular that visually indicates an orientation of the scoop opening within the pipeline with respect to the pipeline; and tightening a compression nut which surrounds the tubular to compress a ferrule which also surrounds the tubular to seal around a smooth outer surface of the tubular to affix the orientation of the scoop opening with respect to the pipeline.

The method wherein the step of tightening further comprises initially tightening the compression nut to form an initial seal prior to the step of orienting the scoop opening and then after the orientation continuing to tighten the compression nut to affix the orientation of the scoop opening with respect to the pipeline to align the scoop opening with an axis of the pipeline.

The method wherein the tubular comprises a seamless tubular.

The method further comprising engaging a shoulder on the tubular with a seat in the connector, the tubular and the connector are constructed so that a distance between the scoop opening and the shoulder provides that the scoop opening is Positioned for sampling the fluid flow at least to a middle one third of the pipeline when the shoulder is in engagement with the seat.

A sample scoop mountable to a pipeline for receiving flow from the pipeline, the pipeline being operable for transmitting at least one of liquid oil, oil, gas, or petroleum products, the sample scoop comprising: a tubular comprising a first tubular portion adjacent a scoop end; and
a tubular to pipe connector that seals the tubular and the first tubular portion with respect to the pipeline when the sample scoop is mounted to the pipeline, the tubular being without threads in the region of the tubular to pipe connector; and a bend on an end most surface of the scoop end in the first tubular portion and a corresponding centerline of the tubular to form a scoop opening at the scoop end, the bend comprising a bend radius with a range between two times and four times a diameter of the first tubular portion.

A sample scoop mountable to a pipeline for receiving flow from the pipeline, comprising: a single seamless pipe comprising a first tubular portion adjacent a scoop end; and a scoop bend radius at the scoop end of the first tubular portion of between two times and four times a diameter of the scoop end.

The sample scoop comprising an opening in the scoop end that forms a scoop face, the scoop face comprising at least a scoop face portion that is coaxial with a surface of the first tubular portion.

The sample scoop comprising a second tubular portion of the single seamless pipe, the second tubular portion comprising an increased diameter as compared to the first tubular portion with a shoulder between the first tubular portion and the second tubular portion.

The sample scoop further comprising a mark on the second tubular portion that is aligned with a center of the scoop face.

The sample scoop further comprising a fitting with a compression nut, the fitting with the compression nut being operable to seal around the single seamless pipe while at least initially permitting rotation of the scoop end with respect to the pipeline, the compression nut being tightenable to thereby affix an orientation of the scoop end within the pipeline.

A scoop mountable to a pipeline for receiving flow from the pipeline, comprising: a single seamless pipe comprising a first tubular portion adjacent a scoop end; an opening in the scoop end that forms a scoop face, the scoop face comprises an outline that defines a plane that opens laterally with respect to the first tubular portion, the plane being parallel to an axis of the tubular; and a bend in the single seamless pipe leading to the opening.

The scoop wherein the plane comprises at least a plane portion that is substantially collinear to one side of the tubular.

The scoop wherein a line perpendicular to the plane is perpendicular to an axis of the tubular.

The scoop wherein the scoop face is substantially elliptical.

The wherein a smaller axis of the elliptical face is substantially equal to an internal diameter of the tubular.

The scoop with a scoop bend radius at the scoop end of the single seamless pipe with a bend radius of between two times and four times a diameter of the scoop end.

The scoop wherein a larger axis of the elliptical face varies with respect to the bend radius.

The sample scoop further comprising a non-resilient seal and a fitting with a compression nut, the non-resilient seal and the fitting with the compression nut being operable to seal around the single seamless pipe while at least initially permitting rotation of the scoop end with respect to the pipeline prior to tightening the compression nut to thereby affix an orientation of the scoop end within the pipeline.

A sample scoop mountable to a pipeline receptacle for receiving flow from the pipeline, comprising a tubular defining a scoop face opening laterally with respect to an axis through the tubular, the tubular being configured for sampling the flow from the pipeline; a first seal operable to seal around the tubular while at least initially permitting rotation of the tubular with respect to the pipeline to permit an orientation of the scoop face with respect to the pipeline, the first seal comprising a compression nut, the scoop face being fixed in the orientation as the compression nut is tightened; and a pipe connector attachable to the pipeline receptacle, the pipe connector further comprising threads that form a second seal between the pipe connector and the pipeline receptacle.

The sample scoop wherein the first seal comprises a ferrule seal.

The sample scoop wherein the tubular comprises a first tubular portion comprising and a second tubular portion with an outer diameter larger than the first tubular portion to form a shoulder between the first tubular portion and the second tubular portion, a seat formed adjacent the pipe connector and the first seal, the shoulder being adapted to mount on the seat.

The sample scoop further comprising an alignment marker on the tubular visible from outside the pipeline that indicates an orientation of the scoop face with respect to the pipeline.

The scoop system further comprising a tubular to pipe connector that comprises the pipe connector, the first seal, a fitting, and the compression nut.

The scoop system wherein the tubular is smooth and without threads in the region of the first seal.

The scoop system wherein the fitting engages the tubular to seal around the tubular without threads as the compression nut is tightened.

DETAILED DESCRIPTION OF THE INVENTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

FIG. 1A and FIG. 1B show a bended scoop design 10 that comprises a single seamless pipe or tubular with first tubular portion 12 adjacent scoop end 14. Second tubular portion 28 has a larger outer diameter 30 than outer diameter 26 of first tubular portion 12.

One possible method of the present invention involves machining the single tubular pipe to reduce the original pipe stock diameter to outer diameter 30 of second tubular portion 28. Then further machining reduces the outer diameter of first tubular portion 12 to outer diameter 26. Shoulder 32 is formed between first tubular portion 12 and second tubular portion 28. The scoop end is then bent as shown to provide scope face 16 that is oriented laterally and preferably perpendicular with respect to centerline 24 as indicated by line scoop face centerline 19.

Accordingly, the bending of first tubular portion 12 of scoop design 10 results in forming scoop face 16. In one embodiment, scoop face 16 provides opening 22 (See FIG. 1A) that is preferably perpendicular and at least angled with respect to tubular centerline 24 as indicated by the perpendicular scoop face centerline 19. At least a portion and preferably the centerline of scoop face 16 is coaxial with a surface of the straight portion of first tubular portion 12. Scoop face 16 comprises outline 36 that preferably defines a plane that is parallel to axis 24. Outline 36 can be elliptical or substantially elliptical in shape. A smaller axis 21 of the ellipse of outline 36 is substantially equal to an internal diameter 38 of scoop design 10. The larger axis of the ellipse varies with respect to the bend radius.

First tubular portion 12 is bent to provide bend radius 18 as shown in FIG. 1B. Bend radius 18 is between two times and four times of scoop 10 and preferably two and four times that of outer diameter 30 of second tubular portion 28 although conceivably between two and four times outer diameter 26 of first tubular portion 12. In another embodiment, bend radius 18 may be between two and three times outer diameter 26. In another embodiment, bend radius 18 may be between 2.3 and 2.7 times outer diameter 26 and/or may be within a smaller range or larger range or outside these ranges. The bend radius may vary depending on the outer diameter of first tubular portion 12. The bend radius affects the fluid flow characteristics and these ranges have been found to provide the best fluid flow through bended sample scoop design 10.

While the features of the scoop face 16 are defined herein in terms of geometrical features such as planes, ellipses, perpendicular, and so forth, it is understood that the features are not geometrically perfect and could have variations, e.g., with 2 and/or to 5 and/or to 10 and/or to 20 range degree variations and any range there between. However, the design may fall outside these ranges and may include corresponding non-linearities.

Scoop 10 provides mark 34 shown in FIG. 1A that is aligned with the center of scoop face 16. This allows alignment of scoop face 16 with respect to the center line of the pipeline as discussed with respect to FIG. 2. In other words, scoop 10 can be rotated to provide that mark 34 is in-line with the axis of the pipeline, whereupon the scoop is fixed in that orientation as discussed hereinbefore.

Scoop design 10 is preferably provided in three different sizes with outer diameter 30 ranging from one inch to one and one-half inches.

FIG. 2A shows the scoop design 10 mounted in an orientable or alignable sampling assembly 200 that permits alignment of scoop face 16 with respect to the pipeline axis and flow arrow 218. In this way, flow or fluid pressure into scoop face 16 can be maximized. Orientable sampling assembly 200 is believed to be yet another significant improvement over the prior art.

Alignable or orientable sampling assembly 200 preferably utilizes tubular to pipe connector 202, which is commercially available off the shelf, in a highly unique manner. Pipe connectors require threads. Tubular to pipe connector 202 comprises a tubular pipe connection with ferrule seals 218, 220 and threaded pipe connection with threads 208. Accordingly a tubular to threaded connection comprises a connection from a non-threaded cylinder to a threaded connection. Tubular to pipe connector 202 comprises compression nut 204, which is threadably securable to pipe connector 206 utilizing threads 222. Pipe connector 206 provides pipe connection with threads 208 to receptacle 210, which is provided on pipe 212. Receptacle 210 utilizes seal 214 with pipe 212, which can be one of three sanctioned connections 1) pipe threads & sealant; 2) socket weld or 3) butt-weld. Valve 216 may be secured to an upper end of scoop design 10 and may be utilized to provide samples of the pipe fluid as desired.

FIG. 2B shows an enlarged view of tubular to pipe connector 202. It will be seen that compression nut 204 can be utilized to compress ferrules 218 and 220 for sealing around the tubular body of scoop design 10. As compression nut 204 is tightened by rotation on threads 222, a seal is formed, which may be referred to as a first seal in the claims, around the tubular body of scoop design 10. Further, threads 208, which may be referred to as a second seal in the claims, are tightened to provide a seal between receptacle 210 and pipe connector 206. Shoulder 32, shown in FIGS. 1A and 1B, seats onto seat 232 formed within tubular to pipe connector 202.

In operation of one embodiment of alignment or orientation, scoop 10 is placed in tubular to pipe connector 202 until shoulder 32 of scoop 10 engages seat 232 in tubular to pipe connector 202. Scoop 10 can then be rotated to orient scoop face 216 within pipe 212 for receiving flow in pipe 212 as indicated by arrow 218. This is accomplished utilizing mark 34 shown in FIG. 1A that is aligned with the center of scoop face 216. Once scoop face 216 is aligned with respect to pipe 212, then compression nut 204 can be tightened to seal around the tubular body of scoop 10. Two scoops like that of FIG. 2A may be used to provide a measurement loop for bi-directional flow out of pipe 212 and then return the flow to the pipe after measurements are made as discussed hereinafter.

FIG. 3A, FIG. 3B, FIG. 3C and FIG. 3D show aspects of retractable scoop and yoke design pipeline scoop 300 in accord with one embodiment of the present invention. Retractable pipeline scoop 300 preferably utilizes scoop design 10, which allows easy movement into and out of pipeline 304 because scoop design 10 has the same OD as a single tubular. While other types of scoops could possibly be utilized, scoop design 10 is probably the best type of scoop for use in retractable pipeline scoop 300.

As discussed herein with other embodiments of the invention, two retractable pipeline scoops could be connected together to form a flow loop for to measure pipeline fluid with a densitometer, flow meter, prover, and/or takes samples as desired.

Unlike prior art scoops which may be time consuming to remove when a pig is sent down the pipeline, retractable pipeline scoop 300 can be easily retracted from the pipeline and inserted into the pipeline without requiring loss of the seal. Pipeline downtime is therefore greatly reduced.

In this embodiment, upper yoke 305 and lower yoke 304 are mounted on yoke screws 306 and 308. Yoke screws 306 and 308 extend through openings 310 and 312 in overall yoke design 302 shown in FIG. 3D. Scoop 10 extends through but is fixed to opening 314 in upper yoke 305. Openings 311 and 313 in upper yoke 305 are threaded. The corresponding openings 316, 318 are not threaded. Opening 320 in lower yoke 304 allows scoop 10 to slidably move therethrough as seen in FIG. 3A, FIG. 3B, and FIG. 3c.

Accordingly, one main difference between upper yoke 302 and lower yoke 304 is that openings 311 and 313 are threaded whereas openings 316 and 318 are not. As well, upper yoke 305 is secured to scoop 10 whereas lower yoke 304 allows scoop 10 to move therethrough and includes an O-ring seal when the tubular to pipe connector sealing is not yet connected (See FIG. 3C) prior to operation as shown in FIG. 3A (scoop removed from pipeline) and FIG. 3B (scoop extended into pipeline).

As yoke screws 306 and 308 are rotated, yoke 305 is urged to move. For manual operation, a few turns can be applied to one yoke screw and then applied to the other yoke screw. The operation could be automated.

Figure 3B:
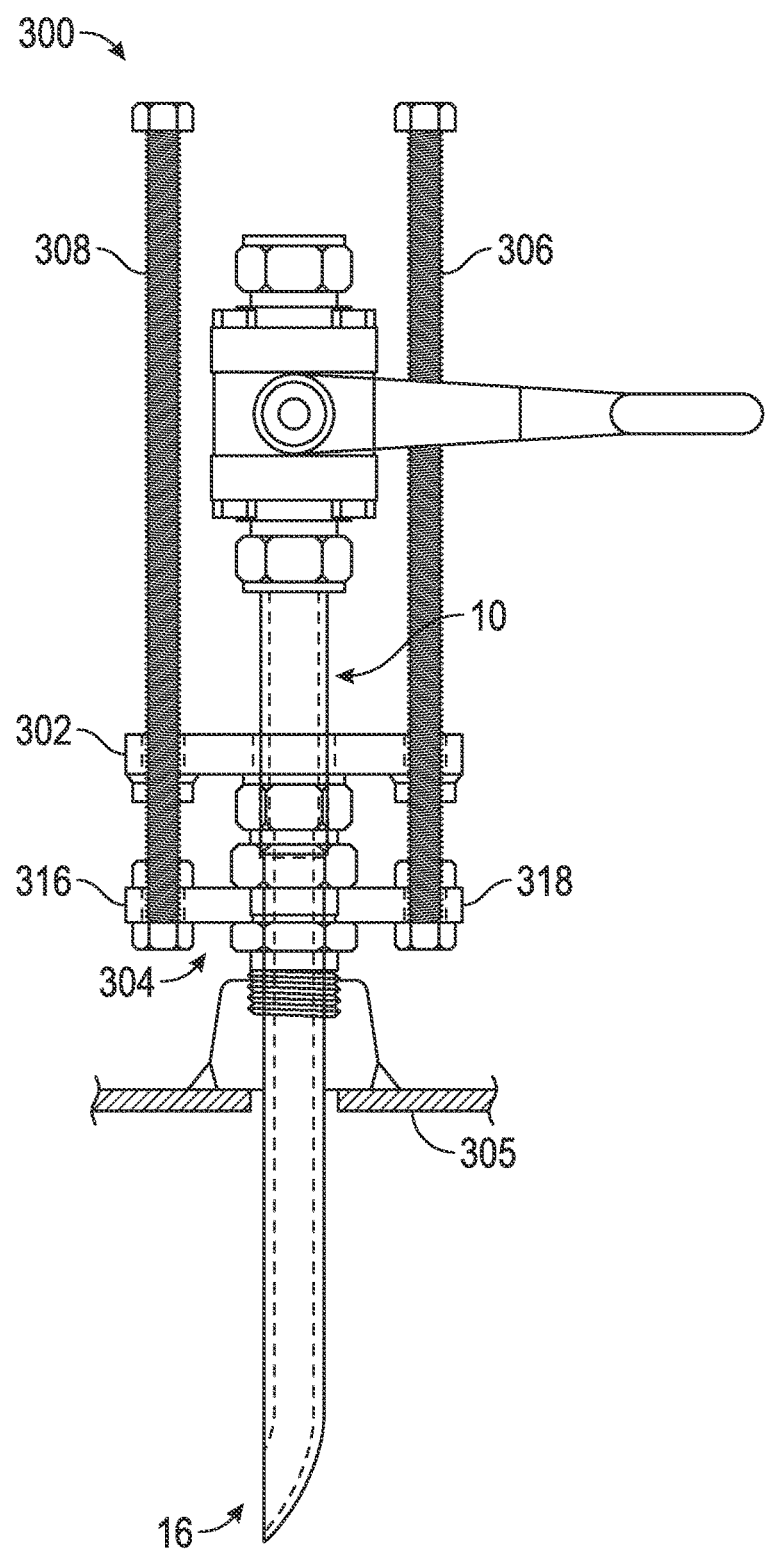
FIG. 3B is a side elevational view, partially in cross-section, showing the retractable scope and yoke design of FIG. 3A in an extended position with respect to a pipeline in accord with one possible embodiment of the present invention.

The sealing of FIG. 2 is utilized during operation as shown in FIG. 3A and FIG. 3B but utilizes O-rings at 320 prior to connection of the tubular to pipe seals as indicated in FIG. 3C. O-rings may comprise suitable resilient O-ring seal material. The O-ring seal preferably utilizes a smoother finish on the scoop pipe surface.

FIG. 3D shows the general plan layout of upper yoke 305 and lower yoke 304 with the differences discussed hereinbefore for openings 310, 312, and 315.

FIG. 4, FIG. 5, FIG. 6, FIG. 9A, and FIG. 9B show various compact tandem scoop configurations that utilize two scoops oriented in opposite directions on a single flange in the pipeline for sampling and/or densitometer and/or flow meter fluid flow loops. The measurement flow loops discussed hereinafter provide sufficient flow of fluid from the pipeline without the need for differential pressure devices (such as pumps or the like), thereby significantly reducing the size, complexity, and fluid contamination. In a preferred embodiment, the compact sampling loops utilize scoop 10 discussed hereinbefore but the present invention is not limited to those scoop designs.

Figure 4:
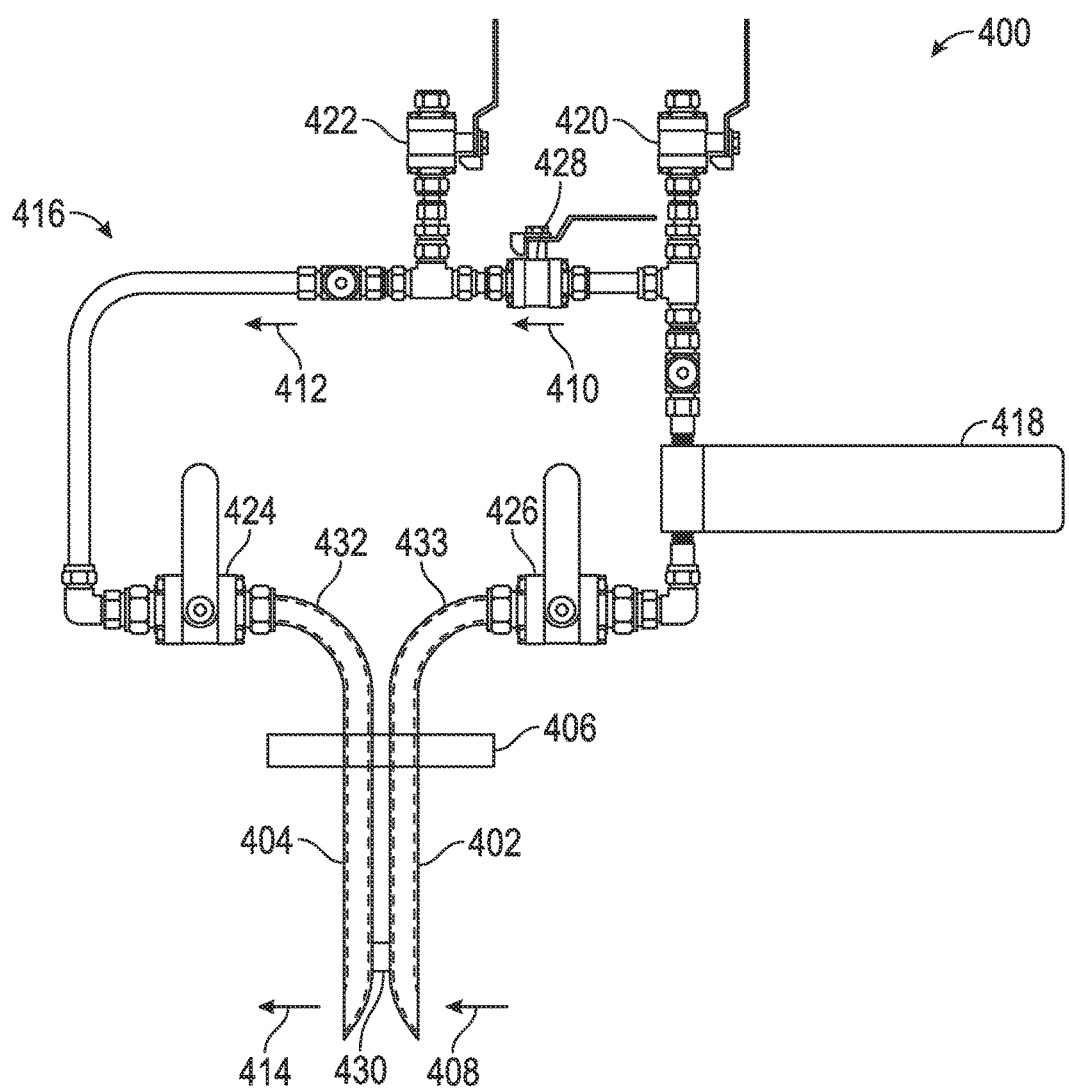
FIG. 4 is a side elevational view, partially in hidden lines, showing one type of compact sampling and/or densitometer loop with tandem scoops in accord with one possible embodiment of the present invention.

In FIG. 4 there is shown flow axis aligned tandem scoop system 400 mounted to a single flange 406. Scoops 402 and 404 extend through top flange 406, which may be a typical 3"-600# mounting flange. Scoops 402 and 404 are sealed by top flange 406, which itself is sealingly mounted to the pipeline. Flow proceeds through flow loop 416 as indicated by arrows 408, 410, 412, and 414 whereby flow is taken out of the pipeline and then returned to the pipeline. Well known configurations of the flow loop may comprise densitometer 418, sampling valves 420, 422, and flow control valves 424, 426, and 428. As per standard API requirements, scoops 402 and 404 are designed to have a length that access the middle $\frac{1}{3}^{rd}$ of flow.

In tandem scoop system 400, scoops 402 and 404 are positioned upstream and downstream of each other in line with the axis of the pipe and oriented in opposite directions. Scoops 402 and 404 are mounted into a single flange 405 and secured together at a lower end by mounting member 430. Bends 432 and 433 are provided to allow the various connections to be made to valves 426 and 424. Accordingly, an entire sampling system can extend through a single flange mounting.

Figure 6:
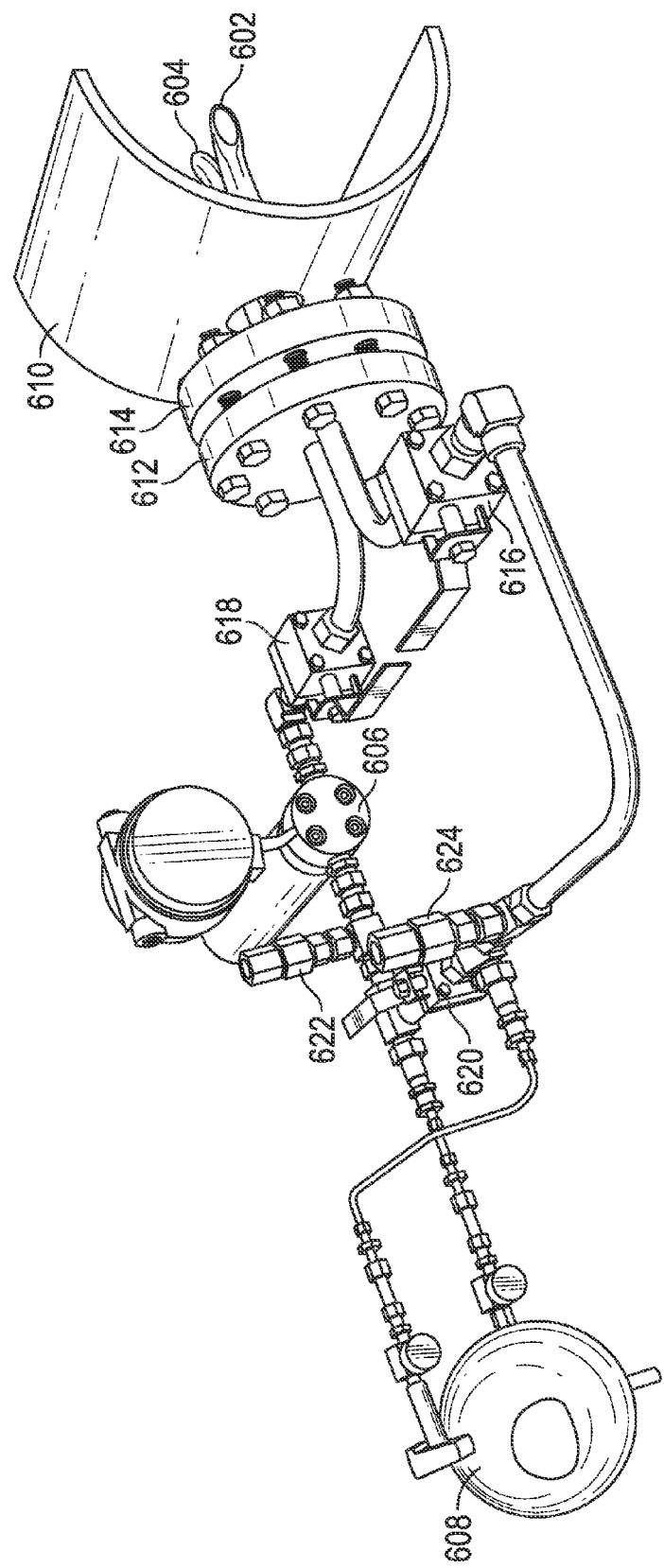
FIG. 6 is a perspective view showing a prover, sampling and/or densitometer loop with tandem scoops in accord with one possible embodiment of the present invention.

FIG. 6 shows a perspective view of flow axis aligned scoops 602 and 604 with connections to densitometer 606 and prover 608. A half portion of pipeline 610 is provided with flange 612 secured to flange mounting 614 provided on pipeline 610. Valves 616, 618, 620, and/or other valves can be used to control fluid flow through the measurement flow loop. Fluid samples can be taken at 622 and 624.

Figure 5:
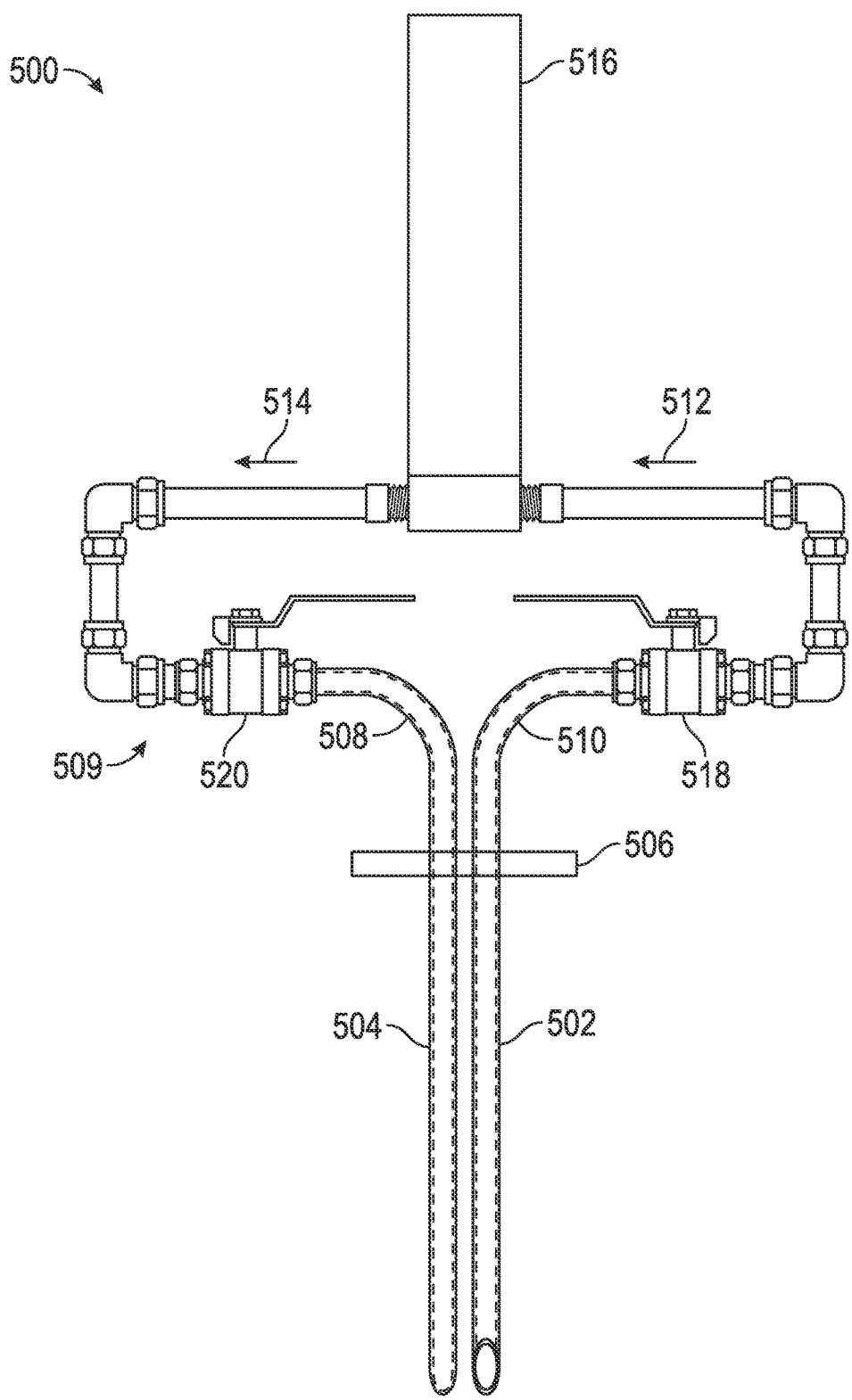
FIG. 5 is a front elevational view, partially in hidden lines, showing another type of compact sampling and/or densitometer loop with tandem scoops in accord with one possible embodiment of the present invention.

Referring now to FIG. 5, perpendicular mount tandem scoop system 500 provides scoops 502 and 504 positioned side by side or perpendicular with respect to the axis of the pipeline. In this embodiment flange 506 may comprise a 2"-150# mounting flange. Bends 508 and 510 permit connection to flow loop 506, which in this embodiment comprises densitometer 516 and valves 518, 520. Flow may proceed into and out of the pipeline in a direction through flow loop 509 with flow direction indicated by arrows 512 and 514.

Figure 9A:
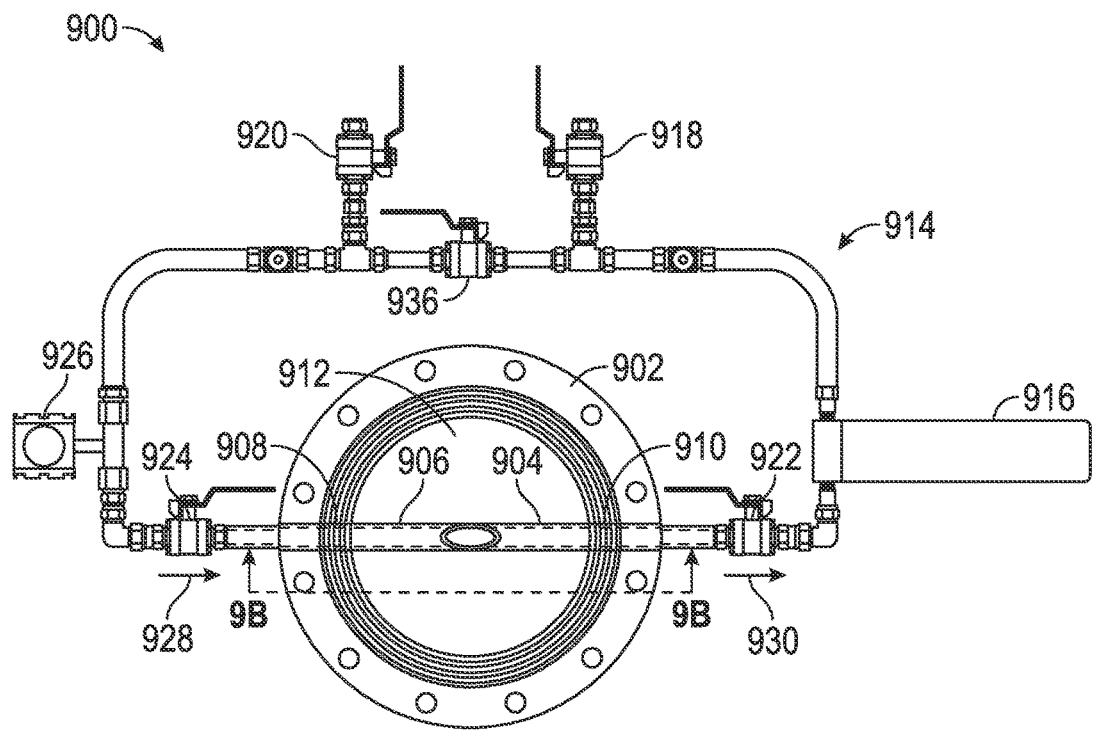
FIG. 9A is a side elevational view of wafer mounted tandem scoops that provides a sampling and/or densitometer and/or flow meter loop in accord with one possible embodiment of the present invention.
Figure 9B:
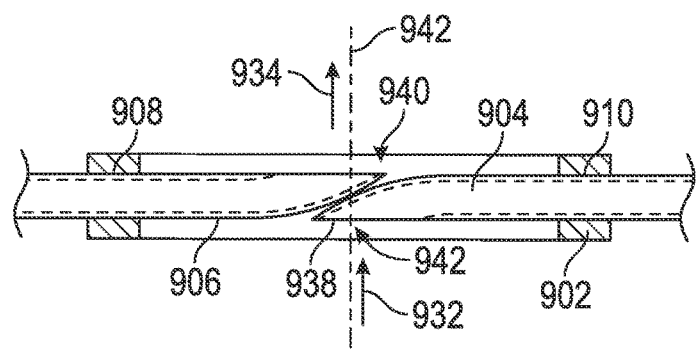
FIG. 9B is a cross-sectional view of FIG. 9A along lines A-A in accord with one possible embodiment of the present invention.

FIG. 9A and FIG. 9B show wafer mount tandem scoop system 900. In two possible examples, wafer flange 902 may comprise a 12" 150# or 10" 900# wafer flange. The wafer flange can be mounted between flanges in the pipeline so that wafer flange 902 surrounds the flow area going through the pipeline. In this example, scoops 904 and 906 are axially aligned with respect to the pipeline axis and extend from opposite directions and from opposite sides of wafer flange 902. Scoops 904 and 906 are sealed and mounted within wafer flange 902 as indicated at 908 and 910 and are essentially in-line with plane 912 defined by wafer flange 902.

In wafer mount system 200, it is not necessary to provide a bend in scoops 904 and 906. Flow loop 914 can comprise densitometer 916, sampling valves 918, 920, flow meter 926, and control valves 922, 936, 928. Fluid flows through loop 914 in the direction indicated by arrows 928 and 930. As indicated in FIG. 9B, flow proceeds out of the pipeline in the direction shown by arrow 934 and into the pipeline in the direction indicated by arrow 932. Scoop faces 938 and 940 are axially aligned with pipeline centerline 942.

Accordingly, the present invention provides three compact tandem scoop system 400, 500, and 900 that mount two scoops to a single flange.

Figure 7:
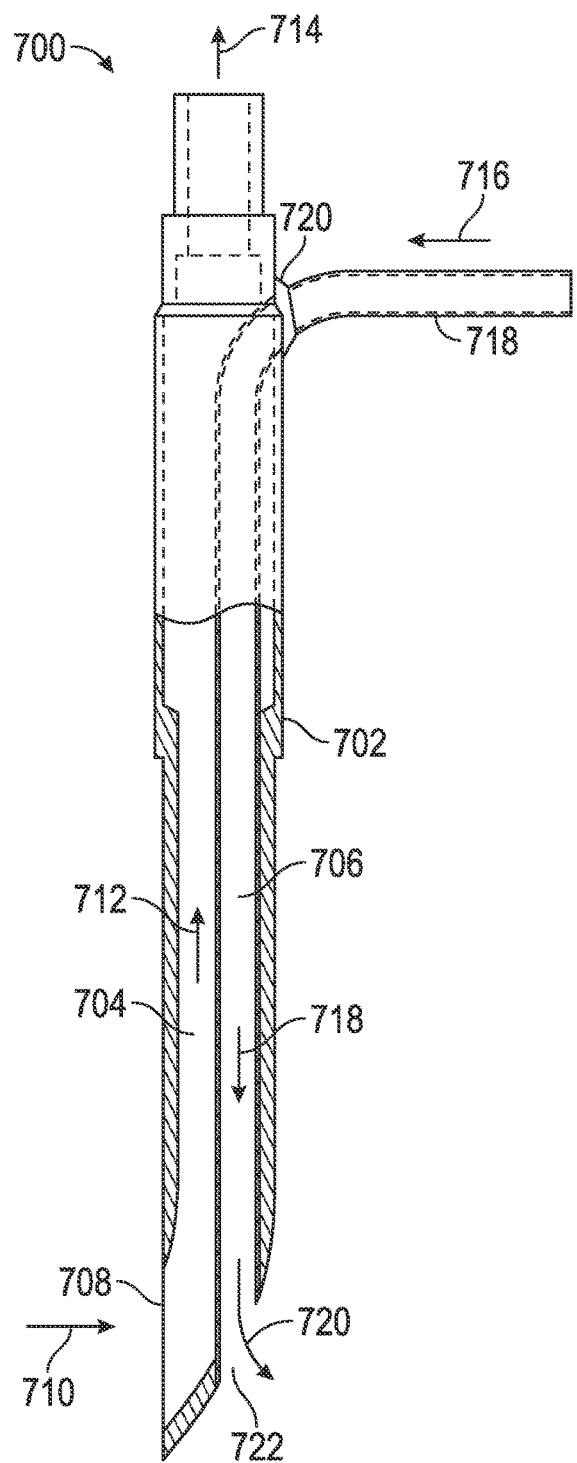
FIG. 7 is side view, partially in hidden lines of a first type of bidirectional flow single tubular flow scoop that provides a sampling and/or densitometer and/or prover loop in accord with one possible embodiment of the present invention.
Figure 8:
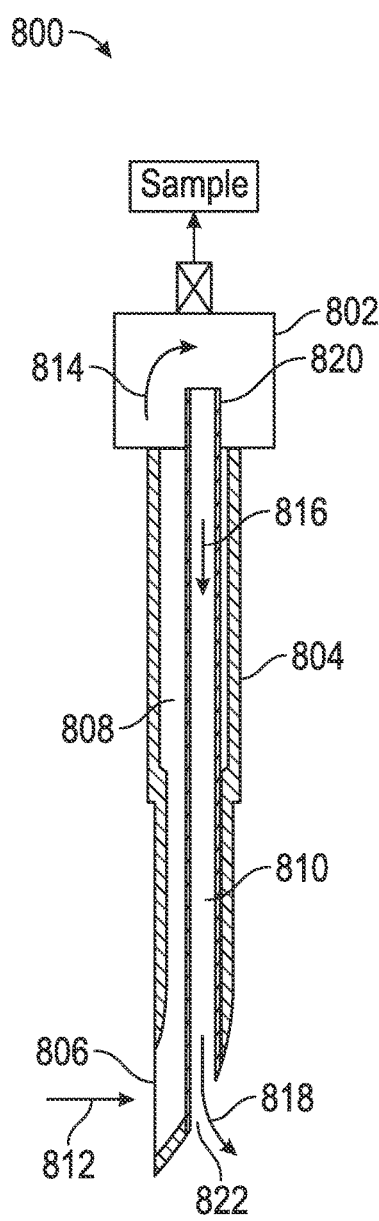
FIG. 8 is a side view, partially in cross-section, showing a second type of bidirectional flow single tubular flow scoop with a mixing chamber in accord with one possible embodiment of the present invention.

FIG. 7 and FIG. 8 show bi-directional flow scoops formed within a single pipe. Bi-directional flow loop scoop 700 provides a single tubular scoop that can be utilized to provide a flow loop for density, proving, sampling, and the like as discussed hereinbefore. Bi-directional mixing scoop 800 provides a single tubular scoop that can be utilized to provide a mixing chamber with continually refreshed fluid so that the sample is representative of fluid in the pipeline at the time the sample is taken avoiding the problems of trapped sample at the sampling valve as discussed hereinbefore.

Bi-directional flow loop scoop 700 utilizes single pipe 702 with two separate internal flow paths 704 and 706. The external shape of single pipe 702 is similar or the same as described by scoop 10 discussed hereinbefore so tubular to pipe connector can be utilized for sealing and orientation. Flow proceeds from the pipeline into scoop face 708 as indicated by arrow 710. Fluid then flows as indicated by arrow 712. As indicated by arrow 714, flow goes through a measuring loop, which may be similar to that discussed hereinbefore including a densitometer, prover, sample connections, valves, and the like. Flow then returns as indicated by arrow 716 through tube 718 which enters pipe 702 and is sealed at seal 720. Flow then continues through flowline 706 as indicated by arrow 718 and exits back into the pipeline through opening 722 as indicated by arrow 720. The sealing can be the same as discussed hereinbefore with respect to FIG. 2 utilizing a compression nut that allows orientation of scoop face 708. Bi-directional scoop 700 could also be utilized with the retractable yoke design 300 discussed hereinbefore to provide a retractable bi-directional measurement flow loop.

FIG. 8 provides a single pipe bi-directional scoop 800 that provides a mixing chamber 802 which is continuously refreshed. Prior art sampling systems that utilize a scoop suffer from the problem that stale fluid accumulates therein. Thus, fluid taken at a particular moment may not be representative of fluid in the pipeline. Since the samples are often timed, this could be problematic in verifying that the sample is valid.

Scoop 800 is comprised of single pipe 804. Scoop 800 may be sealed/oriented as discussed with respect to FIG. 2A and FIG. 2B as discussed with respect to FIG. 7 or using other seals as desired. Fluid enters scoop face 806 from the pipeline as indicated by arrow 812. The fluid travels up flow path 808 and enters mixing chamber 802 as indicated by arrow 814. The fluid in mixing chamber 802 is thereby continuously refreshed. Fluid exits mixing chamber 802 via tube 820 and flows in the direction of arrow 816 through flow path 810. Fluid exits single pipe 804 as indicated by arrow 888 through opening 822.

Accordingly, the present invention provides a highly desirable scoop design 10 as indicated in FIG. 1A and FIG. 1B, a seal and orientation apparatus as indicated in FIG. 2A and FIG. 2B, a retractable scoop design shown in FIG. 3A, FIG. 3B, FIG. 3C, FIG. 3D, compact single flange bi-directional tandem mounted scoops as indicated by FIG. 4, FIG. 5, FIG. 6, and FIG. 9A, and single pipe bi-directional scoops as indicated by FIG. 7 and FIG. 8.

The foregoing description of the preferred embodiments of the invention has been presented for purposes of illustration and description only. It is not intended to be exhaustive or to limit the invention to the precise form disclosed; and obviously many modifications and variations are possible in light of the above teaching. Such modifications and variations that may be apparent to a person skilled in the art are intended to be included within the scope of this invention as defined by the accompanying claims.

The invention claimed is:

1. A sample scoop mountable to a pipeline for receiving flow from said pipeline, said pipeline being operable for transmitting at least one of liquid oil, oil, gas, or petroleum products, said sample scoop comprising:
   a tubular comprising a first tubular portion adjacent a scoop end, said scoop end being insertable into said pipeline to receive a sample of said at least one of liquid oil, oil, gas, or petroleum products from said pipeline; and
   a bend on an endmost surface of said scoop end and a corresponding centerline of said tubular to form a scoop opening at said scoop end, said bend comprising a bend radius with a range between two times and four times a diameter of said first tubular portion, said opening in said scoop end forms a scoop face, said scoop face comprising at least a scoop face portion that is coaxial with a straight portion of said first tubular portion, said scoop face is elliptical in shape.

2. The sample scoop of claim 1, comprising a second tubular portion of said tubular, said second tubular portion comprising an increased diameter as compared to said first tubular portion with a shoulder between said first tubular portion and said second tubular portion.

3. The sample scoop of claim 2, further comprising a mark on at least one of said first tubular portion or said second tubular portion that is aligned with said scoop opening that visually indicates an orientation of said scoop opening with said pipeline when said sample scoop is mounted to said pipeline.

4. The sample scoop of claim 3, further comprising a compression nut and ferrule, said compression nut and said ferrule being mounted in surrounding relationship with said first tubular portion, said compression nut being operable to seal around said tubular while at least initially permitting rotation of said scoop end with respect to said pipeline, said compression nut being tightenable to thereby affix said orientation of said scoop opening within said pipeline.

5. A sample scoop mountable to a pipeline for receiving flow from said pipeline, said pipeline being operable for transmitting at least one of liquid oil, oil, gas, or petroleum products, said sample scoop comprising:
   a tubular comprising a first tubular portion adjacent a scoop end to receive a sample of said at least one of liquid oil, oil, gas, or petroleum products when inserted into said pipeline;
   an opening in said scoop end that forms a scoop face, said scoop face comprises an outline that defines a plane that opens laterally with respect to said first tubular portion, said plane being parallel to a straight portion of an axis of said first tubular portion;
   a bend in said axis of said first tubular portion leading to said opening; and
   a seal member and a compression nut, said compression nut and said seal member being mounted in surrounding relationship with said first tubular portion, said tubular comprising a smooth surface for sealing with said seal member.

6. The scoop of claim 5 wherein said plane comprises a plane portion that is substantially collinear to one side of said first tubular portion with said straight portion of an axis, said tubular being a seamless tubular.

7. The scoop of claim 5 wherein said scoop face is elliptical.

8. The scoop of claim 7 wherein a smaller axis of said scoop face is substantially equal to an internal diameter of said first tubular portion with said straight portion of an axis.

9. The scoop of claim 8, wherein said bend comprises a bend radius with a range of between two times and four times a diameter of said first tubular portion.

10. The scoop of claim 5 wherein said seal member comprises a ferrule, said ferrule and said compression nut being operable to seal around said tubular while at least initially permitting rotation of said scoop end with respect to said pipeline prior to finally tightening said compression nut to thereby affix an orientation of said scoop end within said pipeline.

11. A sample scoop mountable to a pipeline receptacle for receiving flow from a pipeline, said pipeline being operable for transmitting at least one of liquid oil, oil, gas, or petroleum products, said sample scoop comprising:
  a tubular comprising a bend and defining a scoop opening, said scoop opening being directed laterally with respect to an axis through said tubular, said tubular being sized for insertion through said pipeline receptacle into said pipeline for sampling said flow from said pipeline to receive a sample of said at least one of liquid oil, oil, gas, or petroleum products from said pipeline;
  a first seal comprising a compression nut and a ferrule, said tubular comprising a smooth surface, said compression nut and said ferrule each being mounted in surrounding relationship to said smooth surface of said tubular, said compression nut and said ferrule and said smooth surface cooperating to initially permit rotation of said tubular with respect to said pipeline to permit an orientation of said scoop opening with respect to said pipeline so that said scoop opening is orientable for alignment with an axis of said pipeline, said compression nut, said ferrule, and said smooth surface further cooperating so that said scoop opening is affixed in said orientation as said compression nut is tightened; and
  a connector attachable to said pipeline receptacle, said tubular being sized for insertion through said connector.

12. The sample scoop of claim 11 wherein said ferrule is compressible by said compression nut to form an initial seal with said smooth surface prior to said compression nut being fully tightened while initially permitting rotation of said tubular with respect to said pipeline to permit said orientation of said scoop opening with respect to said pipeline, said orientation with said pipeline maximizing fluid flow or fluid pressure into said scoop opening.

13. The sample scoop of claim 11 wherein said tubular comprises a first tubular portion and a second tubular portion comprising an outer diameter larger than said first tubular portion to form a shoulder between said first tubular portion and said second tubular portion, a seat formed within said connector, said shoulder being adapted to mount on said seat.

14. The sample scoop of claim 11 further comprising an alignment marker on said tubular visible from outside said pipeline to visibly indicate said orientation of said scoop opening with respect to said pipeline.

15. The sample scoop of claim 13 further comprising said tubular and said connector are constructed so that a distance between said scoop opening and said shoulder provides that said scoop opening is positioned for sampling said fluid flow at least to a middle one third of said pipeline when said shoulder is in engagement with said seat.

16. The sample scoop of claim 14 wherein said tubular comprises a seamless tubular and said compression nut and said connector comprise mating threads to connect said compression nut to said connector.

17. The sample scoop of claim 11 wherein said pipeline receptacle comprises threads that mate to corresponding threads of said connector to form a second seal between said connector and said pipeline receptacle.

18. A method of using a sample scoop assembly mountable to a pipeline for receiving a fluid sample from said pipeline, said pipeline supporting fluid flow therethrough, a pipeline receptacle for mounting said sample scoop assembly to said pipeline, said pipeline being operable for transmitting at least one of liquid oil, oil, gas, or petroleum products, said method comprising the steps of:
  attaching a connector to said pipeline receptacle;
  inserting a tubular through said connector and said pipeline receptacle to receive a sample of said at least one of liquid oil, oil, gas, or petroleum products from said pipeline, said tubular comprising a scoop opening that opens laterally with respect to an axis through said tubular;
  after said inserting and said attaching, then orienting said scoop opening with respect to said pipeline utilizing an alignment marker on said tubular that visually indicates an orientation of said scoop opening within said pipeline with respect to said pipeline; and
  tightening a compression nut which surrounds said tubular to compress a ferrule which also surrounds said tubular to seal around a smooth outer surface of said tubular to affix said orientation of said scoop opening with respect to said pipeline.

19. The method of claim 18 wherein said step of tightening further comprises initially tightening said compression nut to form an initial seal prior to said step of orienting said scoop opening and then after said orientation continuing to tighten said compression nut to affix said orientation of said scoop opening with respect to said pipeline to align said scoop opening with an axis of said pipeline.

20. The method of claim 19 wherein said tubular comprises a seamless tubular.

21. The method of claim 18, further comprising engaging a shoulder on said tubular with a seat in said connector, said tubular and said connector are constructed so that a distance between said scoop opening and said shoulder provides that said scoop opening is positioned for sampling said fluid flow at least to a middle one third of said pipeline when said shoulder is in engagement with said seat.

22. A sample scoop mountable to a pipeline for receiving flow from said pipeline, said pipeline being operable for transmitting at least one of liquid oil, oil, gas, or petroleum products, said sample scoop comprising:
  a tubular comprising a first tubular portion adjacent a scoop end, said scoop end being insertable into said pipeline to receive a sample of said at least one of liquid oil, oil, gas, or petroleum products from said pipeline;
  a tubular to pipe connector that seals said tubular and said first tubular portion with respect to said pipeline when said sample scoop is mounted to said pipeline, said tubular being without threads in the region of said tubular to pipe connector; and
  a bend on an endmost surface of said sample scoop and a corresponding centerline of said tubular to form a scoop opening at said scoop end, said bend comprising a bend radius with a range between two times and four times a diameter of said first tubular portion.

23. A sample scoop mountable to a pipeline for receiving flow from said pipeline, said pipeline being operable for transmitting at least one of liquid oil, oil, gas, or petroleum products, said sample scoop comprising:
  a tubular comprising a first tubular portion adjacent a scoop end, said scoop end being insertable into said pipeline to receive a sample of said at least one of liquid oil, oil, gas, or petroleum products from said pipeline;

a bend on an endmost surface of said scoop end and a corresponding centerline of said tubular to form a scoop opening at said scoop end, said opening in said scoop end forms a scoop face, said bend comprising a bend radius with a range between two times and four times a diameter of said first tubular portion; and a mark on at least one of said first tubular portion or a second tubular portion that is aligned with said scoop opening that visually indicates an orientation of said scoop face with said pipeline when said sample scoop is mounted to said pipeline.

24. A sample scoop mountable to a pipeline for receiving flow from said pipeline, said pipeline being operable for transmitting at least one of liquid oil, oil, gas, or petroleum products, said sample scoop comprising:

a tubular comprising a first tubular portion adjacent a scoop end to receive a sample of said at least one of liquid oil, oil, gas, or petroleum products from said pipeline; and a bend in said first tubular portion and a corresponding centerline of said tubular to form a scoop opening at said scoop end, said bend comprising a bend radius with a range between two times and four times a diameter of said first tubular portion.

* * * * *